(12) United States Patent
Hargis et al.

(10) Patent No.: US 11,883,489 B2
(45) Date of Patent: *Jan. 30, 2024

(54) MUCOSAL ADJUVANTS AND DELIVERY SYSTEMS

(71) Applicant: THE BOARD OF TRUSTEES OF THE UNIVERSITY OF ARKANSAS, Little Rock, AR (US)

(72) Inventors: Billy M. Hargis, Fayetteville, AR (US); Neil R. Pumford, Bentonville, AR (US); Marion Morgan, Springdale, AR (US); Srichaitanya Shivaramaiah, Bangalore (IN); Guillermo Tellez-Isaias, Fayetteville, AR (US); Amanda Wolfenden, Pea Ridge, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 483 days.

This patent is subject to a terminal disclaimer.

(21) Appl. No.: 17/021,345

(22) Filed: Sep. 15, 2020

(65) Prior Publication Data

US 2021/0000947 A1 Jan. 7, 2021

Related U.S. Application Data

(63) Continuation of application No. 16/379,535, filed on Apr. 9, 2019, now Pat. No. 10,780,162, which is a
(Continued)

(51) Int. Cl.
| | |
|---|---|
| A61K 39/39 | (2006.01) |
| A61K 8/99 | (2017.01) |
| A61K 31/722 | (2006.01) |
| A61K 35/68 | (2006.01) |
| A61K 39/012 | (2006.01) |
| A61K 39/02 | (2006.01) |
| A61K 39/112 | (2006.01) |
| A61K 39/108 | (2006.01) |
| A61K 39/08 | (2006.01) |
| A61K 39/085 | (2006.01) |
| A61K 39/09 | (2006.01) |
| A61K 39/12 | (2006.01) |
| A61K 39/145 | (2006.01) |
| A61K 39/00 | (2006.01) |
| A61K 31/7004 | (2006.01) |
| C08B 37/08 | (2006.01) |

(Continued)

(52) U.S. Cl.
CPC ............. *A61K 39/39* (2013.01); *A61K 8/99* (2013.01); *A61K 31/7004* (2013.01); *A61K 31/722* (2013.01); *A61K 35/68* (2013.01); *A61K 39/012* (2013.01); *A61K 39/0241* (2013.01); *A61K 39/0258* (2013.01); *A61K 39/0275* (2013.01); *A61K 39/0283* (2013.01); *A61K 39/08* (2013.01); *A61K 39/085* (2013.01); *A61K 39/092* (2013.01); *A61K 39/099* (2013.01); *A61K 39/12* (2013.01); *A61K 39/145* (2013.01); *A61K 39/155* (2013.01); *C08B 37/003* (2013.01); *C08L 5/08* (2013.01); *A61K 2039/521* (2013.01); *A61K 2039/523* (2013.01); *A61K 2039/5252* (2013.01); *A61K 2039/54* (2013.01); *A61K 2039/542* (2013.01); *A61K 2039/552* (2013.01); *A61K 2039/55505* (2013.01); *A61K 2039/55544* (2013.01); *A61K 2039/55566* (2013.01); *A61K 2039/55572* (2013.01); *A61K 2039/55577* (2013.01); *A61K 2039/55583* (2013.01); *A61K 2039/575* (2013.01); *A61K 2039/6087* (2013.01); *A61K 2039/62* (2013.01); *C12N 2760/16034* (2013.01); *C12N 2760/16122* (2013.01); *C12N 2760/16134* (2013.01); *C12N 2760/16171* (2013.01); *Y02A 50/30* (2018.01)

(58) Field of Classification Search
None
See application file for complete search history.

(56) References Cited

U.S. PATENT DOCUMENTS

| | | |
|---|---|---|
| 3,501,770 A | 3/1970 | Gale |
| 5,747,475 A | 5/1998 | Nordquist |

(Continued)

FOREIGN PATENT DOCUMENTS

| | | |
|---|---|---|
| JP | 2009263266 | 11/2009 |
| JP | 2010065027 | 3/2010 |

(Continued)

OTHER PUBLICATIONS

Amidi, M., et al., Chitosan-based delivery systems for protein therapeutics and antigens, Drug Deliv. Rev., 2010, pp. 59-82, vol. 62:1.
Asthana, G.S., et al., Mannosylated Chitosan Nanoparticles for Delivery of Antisense Olignucleotides for Macrophage targeting, BioMedResearchinternational, 2014, pp. 133-17, vol. 14:2.
Chaubey, P., et al., Mannose-conjugated chitosan nanoparticles loaded with rifampicin for the treatment of visceral leishmaniasis, Carbohydrate Polymers, 2013, pp. 1101-1108, vol. 101.
Da Hora, VP, et al., Non-toxic derivatives of LT as potent adjuvants. Vaccine 29: 1538-1544, 2011.
Extended European Search Report dated Sep. 28, 2016 for European Patent Application No. 13850423.8.

(Continued)

*Primary Examiner* — S. Devi
(74) *Attorney, Agent, or Firm* — Quarles & Brady LLP

(57) ABSTRACT

Adjuvants comprising chitosan cross-linked with an aldehyde or mannosylated chitosan are provided herein. Methods of making the adjuvants and methods of combining or linking the adjuvants with antigens are also provided. The adjuvant-antigen combinations can be used in vaccine formulations and the vaccine formulations can be used in methods to vaccinate animals against the source of the antigen or to enhance the immune response in a subject.

17 Claims, 14 Drawing Sheets

Related U.S. Application Data continuation of application No. 15/363,281, filed on Nov. 29, 2016, now Pat. No. 10,258,688, which is a continuation of application No. 14/439,536, filed as application No. PCT/US2013/067212 on Oct. 29, 2013, now abandoned.

(60) Provisional application No. 61/719,713, filed on Oct. 29, 2012.

(51) Int. Cl.
  *C08L 5/08* (2006.01)
  *A61K 39/155* (2006.01)

(56) References Cited

U.S. PATENT DOCUMENTS

| | | | |
|---|---|---|---|
| 6,113,901 | A | 9/2000 | Bluestone |
| 8,188,244 | B2 | 5/2012 | La Monica |
| 8,697,087 | B2 | 4/2014 | Rappuoli |
| 10,780,162 | B2 * | 9/2020 | Hargis .......... A61K 39/012 |
| 2008/0085242 | A1 | 4/2008 | Artursson |
| 2009/0028932 | A1 | 1/2009 | Wilson |
| 2010/0061992 | A1 | 3/2010 | Anderson |
| 2010/0137193 | A1 | 6/2010 | Baker |
| 2010/0316715 | A1 | 12/2010 | Andersson |
| 2012/0288552 | A1 | 11/2012 | Harel |
| 2014/0112973 | A1 | 4/2014 | Steinberg |

FOREIGN PATENT DOCUMENTS

| | | |
|---|---|---|
| UA | 5098 U | 2/2005 |
| WO | 1999027960 | 6/1999 |
| WO | 2010067318 | 6/2010 |
| WO | 2011057200 | 5/2011 |

OTHER PUBLICATIONS

Fu, M.L., et al. Regulating effects of Novel CpG Chitosan-nanoparticles on Immune Responses of Mice to Porcine Parathyroid Vaccines. Biomedical and Environmental Sciences. 2006. 19: 315-322.

Guo, Z., et al., The synthesis and antioxidant activity of the Schiffbases of chitosan and carbozymethyl chitosan, Bioorganic & Medicinal Chemistry Letters, 2005, pp. 4600-4603, vol. 15.

Guy, B. The perfect mix: recent progress in adjuvant research. Nature Reviews Microbiology 5: 505-517, 2007.

Hall, L.D., Yalpani, M., Formation of branched-chain, soluble polysaccharides from chitosan. J.C.S. Chem. Comm.833: 1153-1154, 1980.

Jiang, H., et al., The potential of mannosylated chitosan microspheres to target macrophage mannose receptors in an adjuvant-delivery system for intranasal immunization. Biomaterials 29: 1931-1939, 2008.

Hashimoto, M., et al., Gene transfer by DNA/mannosylated chitosan complexes into mouse peritoneal macrophages. Biotechnol. Lett. 28: 815-821, 2006.

Il'Ina, A.V. et al., Obtaining and Study of Monosaccharide Derivatives of Low-Molecular-Weight Chitosan. Applied Biochemistry and Microbiology. 2008. 44(5):551-558.

International Preliminary Report on Patentability in International Patent Application No. PCT/US2013/067212 dated May 14, 2015 (7 pages).

International Search Report and Written Opinion in International Patent Application No. PCT/US2013/067212 dated Feb. 20, 2014 (15 pages).

Jabbal-Gill, I., et al., Chitosan-based delivery systems for mucosal vaccines. Expert Opin Drug Deliv. 9: 1051-1067, 2012.

Jayasree, A., et al., Mannosylated chitosan-zinc sulphide nanocrystals as fluorescent bioprobes for targeted cancer maging. Carbohydrate Polymers 85: 37-43, 2011.

Jyothi, N, et al., Microencapsulation Techniques, Factors Influencing Encapsulation Efficiency: A Review, Internet J. Nanotechnology. 3(1): 1-13, 2008.

Kim, T.H., et al., Mannosylated chitosan nanoparticle-based cytokine gene therapy suppressed cancer growth in BALB/c mice bearing CT-26 carcinoma cells. Mol Cancer Ther. 5: 1723-1732, 2006.

Mutwiri, G. et al., Combination adjuvants: the next generation of adjuvants? Expert Rev Vaccines 10: 95-107, 2011.

Muzzarelli, R.A.A., Chitins and Chitosans as immunoadjuvants and non-allergenic drug carriers, Marine Drugs, 2010, pp. 292-312, vol. 8:2.

Office Action dated Jul. 29, 2016 for U.S. Appl. No. 14/439,536 (14 pages).

Office Action dated Mar. 8, 2016 for U.S. Appl. No. 14/439,536 (13 pages).

Office Action dated May 19, 2017 for U.S. Appl. No. 15/363,281 (9 Pages).

Office Action dated Nov. 30, 2017 for U.S. Appl. No. 15/363,281 (12 Pages).

Sayin, B., et al., Mono-N-carboxymethyl chitosan (MCC) and N-trimethyl chitosan (TMC) nanoparticles for non-invasive vaccine delivery, Inter. J. Pharmaceutics 363: 139-148, 2008.

Tang, Z.X., and Qian, J.Q., Use of Chitosan Gel for the Purification Protein, Braz. Arch. Biol. Technol. 5-: 299-309,2007.

Woo, P.C.Y., et al., Unique immunogenicity of hepatitis B vims DNA vaccine presented by live-attenuated *Salmonella yphimurium*. Vaccine. 2001 (19):2945-2954.

Yalpani et al., "Some chemical and analytical aspects of polysaccharide modifications. 3. Formation of branch-chain, soluble chitosan derivatives," (1984) Macromolecules 17(3): 272-281.

Yalpani, M., and Hall, L.D., Some chemical and analytical aspects of polysaccharide modifications. IV. Electron spin resonance studies of nitroxide-labelled chitin and chitosan derivatives. Can. J. Chem. 62: 975-980, 1984.

Yao, W., et al., Practical synthesis and characterization of mannose-modified chitosan, International Journal of Biological Macromolecules, 2012, pp. 821-825, vol. 50.

Yao, W., et al., Preventative vaccine-loaded mannosylated chitosan nanoparticles intended for nasal mucosal delivery enhance immune responses and potent tumor immunity, Molecular Pharmaceutics, 2013, pp. 2904-2914, vol. 10.

Yu, H. et al., Preparation and Properties of Novel Hydrogels from Oxidized Konjac Glucomannan Cross-Linked Chitosan for in vitro drug Delivery. Macromolecular Bioscience. 2007. 7:1100-1111.

Zhou, X., et al., Controlled release of PEI/DNA complexes from mannose-bearing chitosan microspheres as a potent delivery system to enhance immune response to HBV DNA vaccine. J. Controlled Rel. 121: 200-207, 2007.

* cited by examiner

Fig. 2

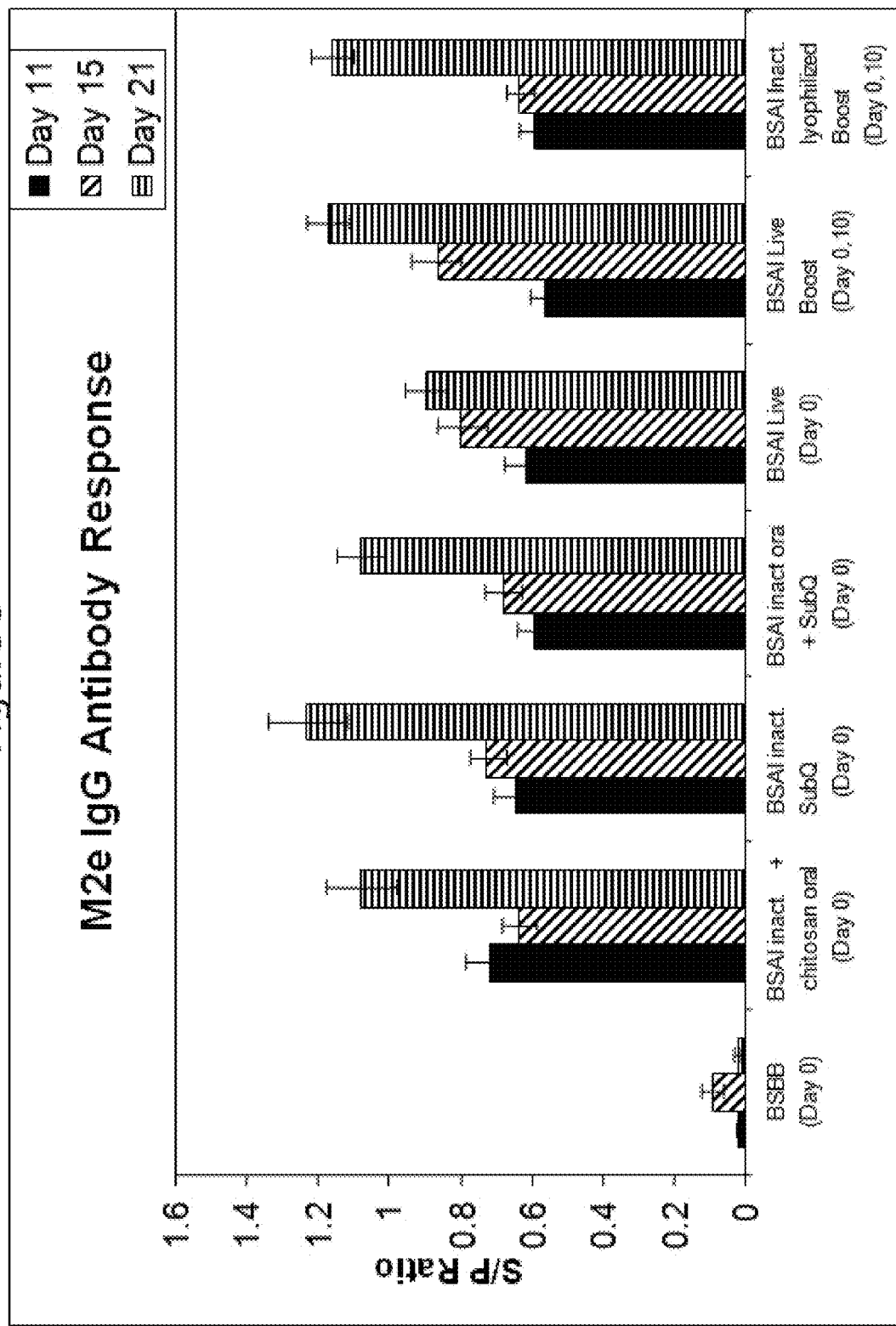

MUCOSAL ADJUVANTS AND DELIVERY SYSTEMS

CROSS-REFERENCE TO RELATED APPLICATIONS

This patent application is a continuation of application Ser. No. 16/379,535, filed Apr. 9, 2019, now U.S. Pat. No. 10,780,162, which application is a continuation of 15/363,281, filed Nov. 29, 2016, now U.S. Pat. No. 10,258,688, which application is a continuation of application Ser. No. 14/439,536, filed Apr. 29, 2015, now abandoned, which application is a national stage filing under 35 U.S.C. 371 of International Application No. PCT/US2013/067212, filed Oct. 29, 2013, which claims the benefit of priority of U.S. Provisional Patent Application No. 61/719,713, filed Oct. 29, 2012, which is incorporated herein by reference in its entirety.

INTRODUCTION

An adjuvant is a pharmacological or immunological agent that modifies the effect of other agents, such as a drug or vaccine. Adjuvants are often included in vaccines to enhance the recipient's immune response to a supplied antigen, while keeping the injected foreign material to a minimum.

Adjuvants do not in themselves confer immunity. Adjuvants can act in various ways in presenting an antigen to the immune system. Adjuvants can act as a depot for the antigen, presenting the antigen over a long period of time, thus maximizing the immune response before the body clears the antigen. Examples of depot type adjuvants are oil emulsions, like Freund's adjuvant. Adjuvants can also act as an irritant which causes the body to recruit and amplify its immune response. The tetanus, diphtheria, and pertussis vaccine, for example, contains minute quantities of toxins produced by each of the target bacteria, but also contains aluminum hydroxide. Aluminum salts are common adjuvants in vaccines sold in the United States and have been used in vaccines for over 70 years.

Chitosan is a linear polysaccharide composed of randomly distributed β-(1-4)-linked D-glucosamine (deacetylated unit) and N-acetyl-D-glucosamine (acetylated unit). It is made by treating shrimp and other crustacean shells with the alkali sodium hydroxide. Chitosan has been used as a carrier for both oral and subcutaneous vaccines with some success. Here we present novel chitosan-based adjuvant formulations which are shown to perform better as adjuvants than the traditionally used Alum adjuvants. In particular, the chitosan-based adjuvants provided herein were effective at stimulating an IgA response.

SUMMARY

Provided herein are adjuvants, vaccine formulations comprising the adjuvants, methods of making the adjuvants and methods of using the adjuvants and vaccine formulations. In particular, chitosan and an antigen may be cross-linked using an aldehyde. In one aspect, a composition comprising 0.5% to 2% of an aldehyde cross-linked chitosan and an antigen is provided. The final concentration of aldehyde in a vaccine composition is less than 0.5%.

In another aspect, an adjuvant composition comprising a carbohydrate linked to chitosan to form a Schiff base is provided. The adjuvant may be combined with an antigen. The carbohydrate may be mannose.

In yet another aspect, vaccine formulations are provided. Vaccine formulations may include the adjuvants provided herein and an antigen. The antigens may be proteins or microbial in nature, suitable microbes include bacteria, yeast, or other fungi, eukaryotic parasites and viruses and may be attenuated, recombinant, killed or otherwise inactivated.

In still another aspect, methods of making the adjuvants and vaccine compositions are provided herein. The chitosan is dissolved in a solution of acetic acid, and an antigen is added to the dissolved chitosan. Finally the antigen and chitosan are combined with an aldehyde such that the final concentration of the aldehyde is between 0.02% and 0.5%. Tris may be added to the adjuvant to quench free aldehydes and result in a more stable adjuvant.

In a still further aspect, methods of enhancing the immune response of a subject to an antigen are also provided. The methods include administering a vaccine formulation comprising an antigen and a chitosan-based adjuvant disclosed herein to the subject. The chitosan-based adjuvant may be an aldehyde cross-linked chitosan or a carbohydrate-linked chitosan.

BRIEF DESCRIPTION OF THE DRAWINGS

FIG. 2 is a graph showing the *Clostridium septicum* IgG antibody response in turkeys following primary vaccination and boost with the indicated vaccine-adjuvant formulations. Different letters indicate significant differences ($p \leq 0.05$).

FIG. 11 is a graph showing the IgG immune response to *Bordetella avium* after a single parenteral vaccination of turkeys with the indicated vaccine-adjuvant formulations. Different letters indicate significant differences ($p \leq 0.05$).

FIG. 12 is a graph showing the IgG immune response to *Bordetella avium* after subcutaneous vaccination with the indicated vaccine-adjuvant formulation of day-of-hatch turkeys followed by a drinking water administration of the same vaccine-adjuvant combination on day 14. The response was measured at day 21. Different letters indicate significant differences ($p \leq 0.05$).

DETAILED DESCRIPTION

Provided herein are adjuvants which include chitosan, vaccine formulations comprising the adjuvants, methods of making the adjuvants and methods of using the adjuvants and vaccine formulations. In summary, a novel adjuvant system that can be used in similar methods to other adjuvants such as those used for parenteral (injection) is described herein. The base molecule involves chitosan, which is a deacetylated form of chitin, the exoskeleton of many invertebrate animals (shrimp, crabs, insects, etc.). Chitosan is considered a generally recognized as safe (GRAS) compound and is used for weight loss, cholesterol reduction, insomnia, and kidney function improvement. Chitosan is also used as an adjuvant used with various mucosal vaccines (Jabbal-Gill et al., 2012), but the chitosans described herein are new and function better than traditional chitosan as shown in the Examples.

Chitosan-protein cross-linked with formaldehyde and carbohydrate-linked chitosan provide a unique adjuvant for oral or parenteral delivery of vaccine antigens. Chitosan has been used as a carrier for both oral and subcutaneous vaccines. In some of the formulations, the antigen is covalently bound to the chitosan by treatment with formaldehyde. In others, the adjuvant system is improved by addition of a carbohydrate (mannose, fucose, and galactose) linked to the chitosan, allowing targeting of the mannose receptors on the antigen presenting cells, thus enhancing the immune response to the chitosan-antigen complex. Both the chitosan-protein cross-linked with formaldehyde and the mannosylated-chitosan protein complex, give a robust immune response by both parenteral and oral (or other mucosal) delivery routes, which is unique for inactivated vaccines.

In one aspect, an adjuvant composition comprising a carbohydrate linked to chitosan to form a Schiff base is provided. The adjuvant may be combined with an antigen. The carbohydrate may be mannose, mannobiose, glucose, galactose or fructose. Other suitable carbohydrates may be used. Without being limited by theory, the carbohydrate is added to the chitosan for the purpose of targeting the chitosan to receptors for these carbohydrates on the surface of antigen presenting cells.

Figures 6, 6A:
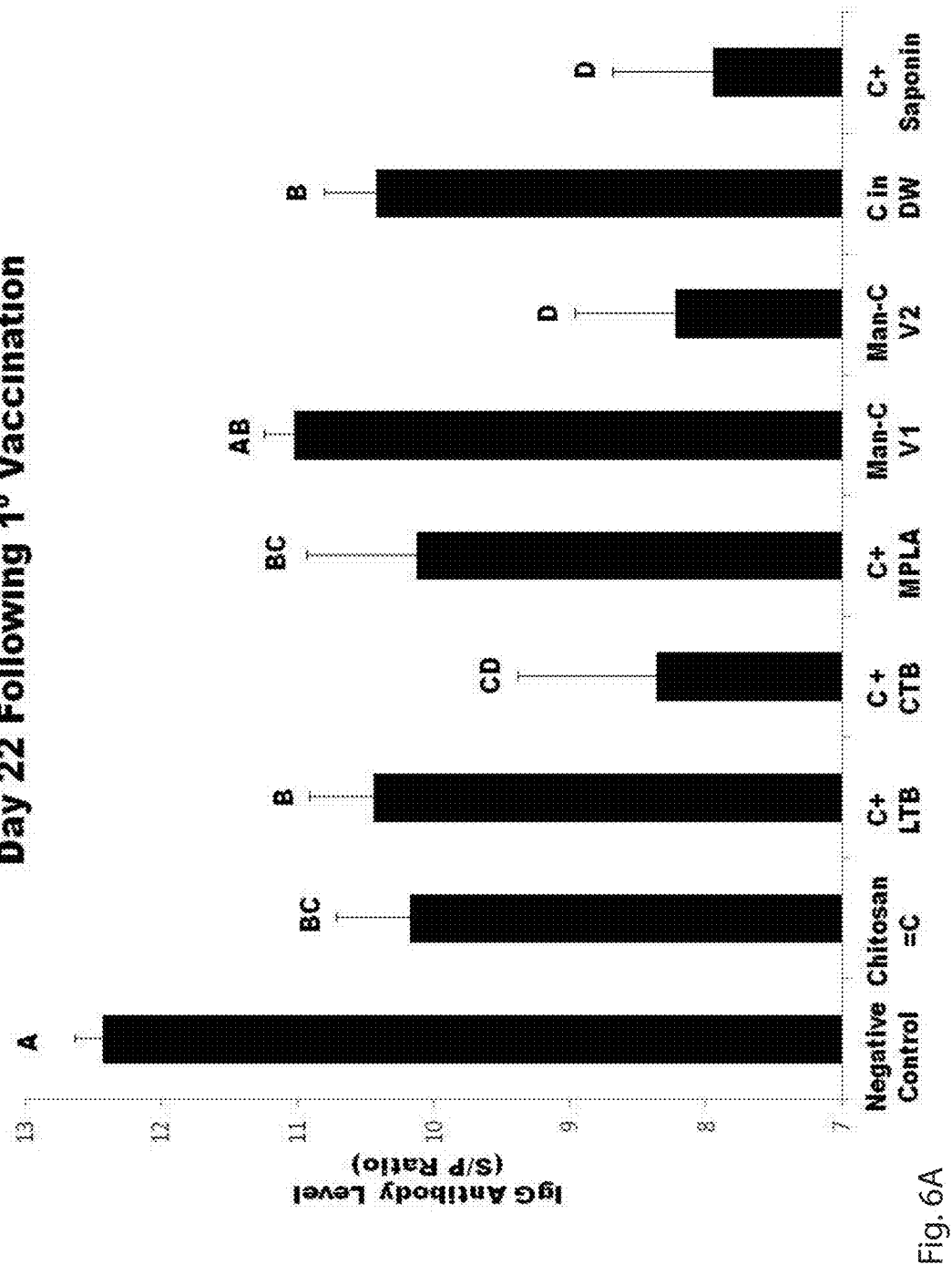
FIG. 6 is a set of graphs showing the IgG (FIG. 6A) and IgA (FIG. 6B) antibody levels against *Salmonella* following primary vaccination and boost with the indicated vaccine-adjuvant formulations measured using a competitive ELISA. Different letters indicate significant differences ($p \leq 0.05$).
Figure 6B:
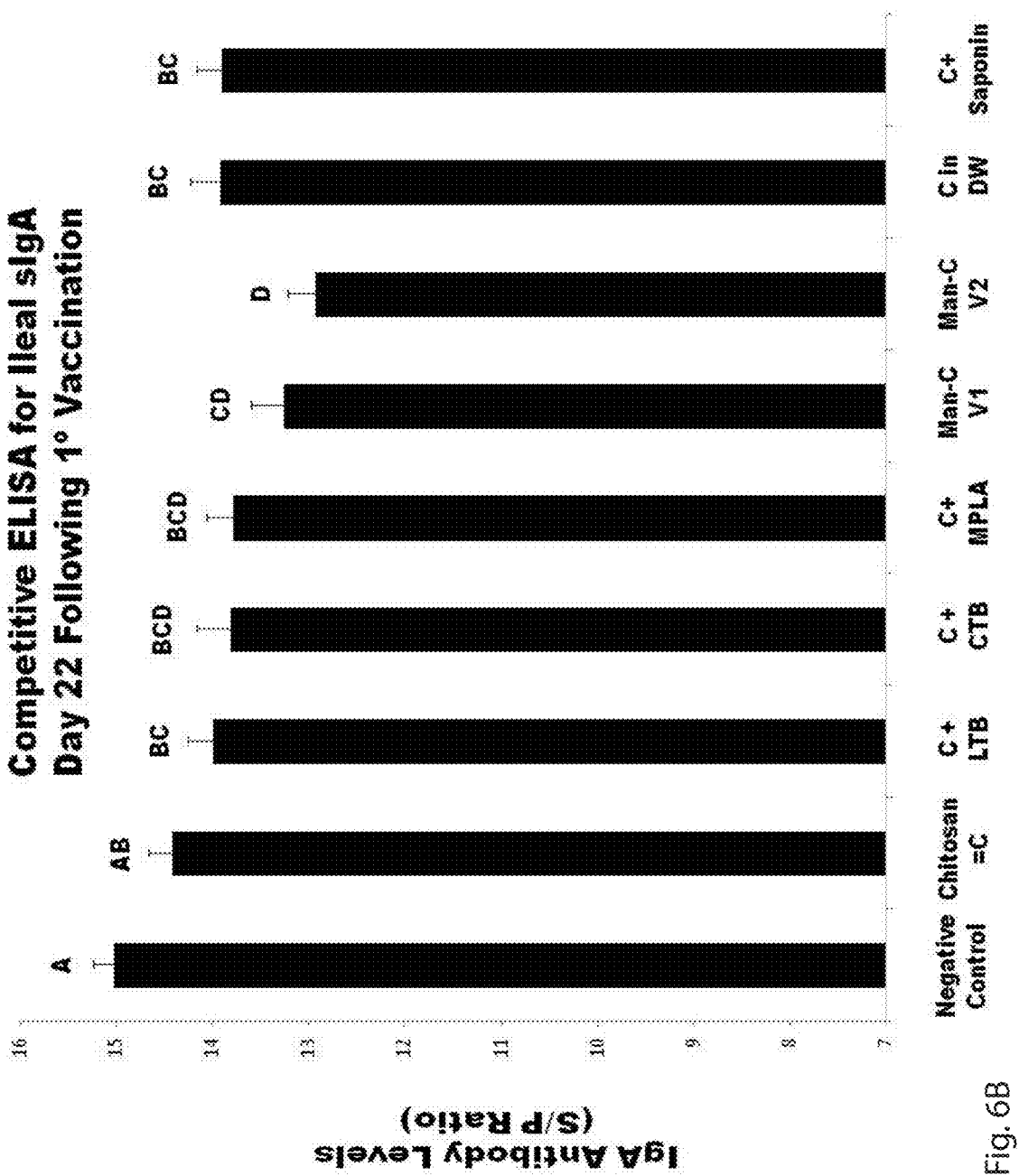
Figure 7:
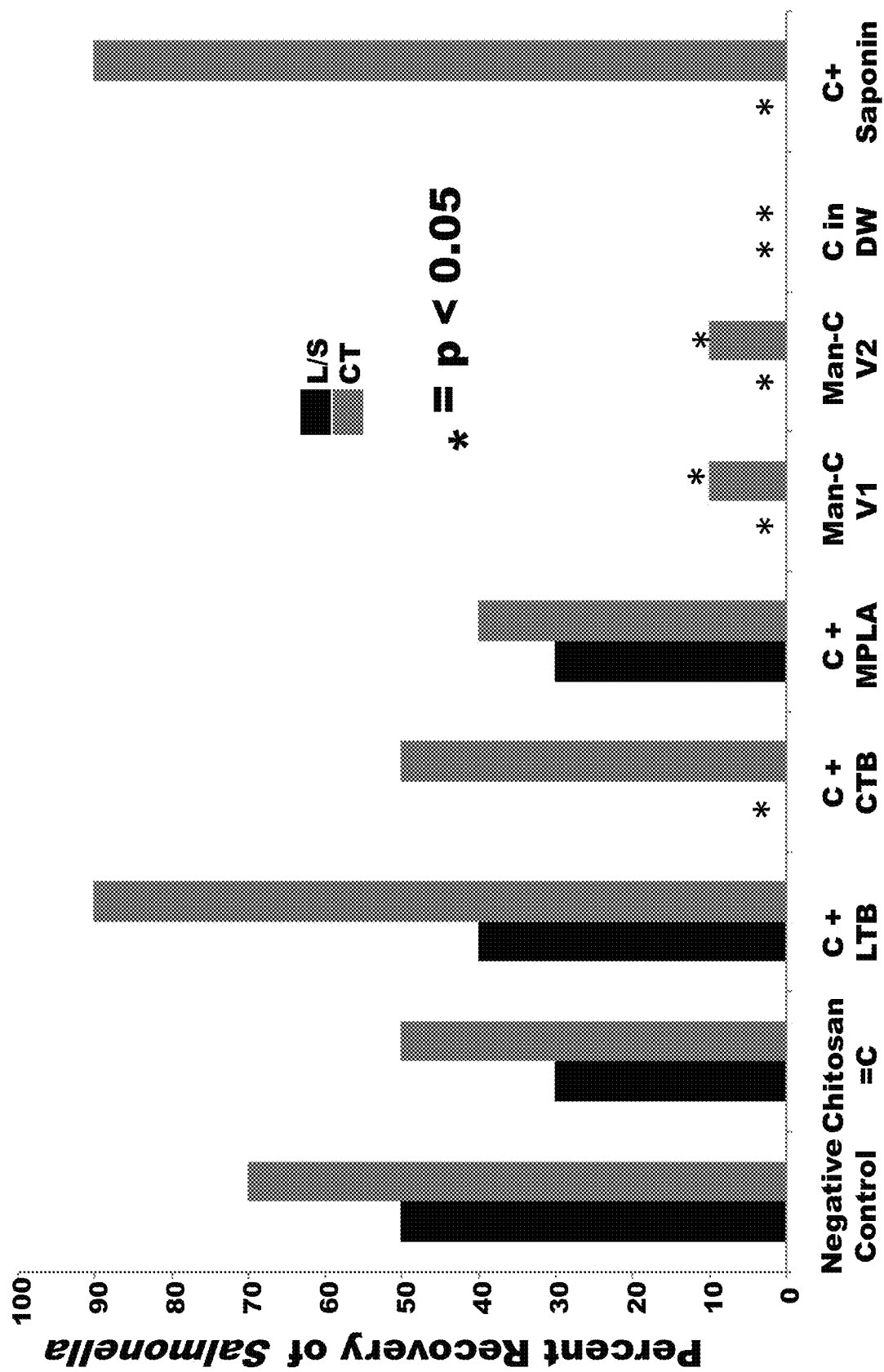
FIG. 7 is a graph showing the percent recovery of *Salmonella* in the liver and spleen (L/S) or cecal tonsils (CT) on day 22 after primary vaccination (day 3 after challenge). The vaccination protocol was the same as that used in FIG. 6 and a * indicates $P < 0.05$.
Figure 8:
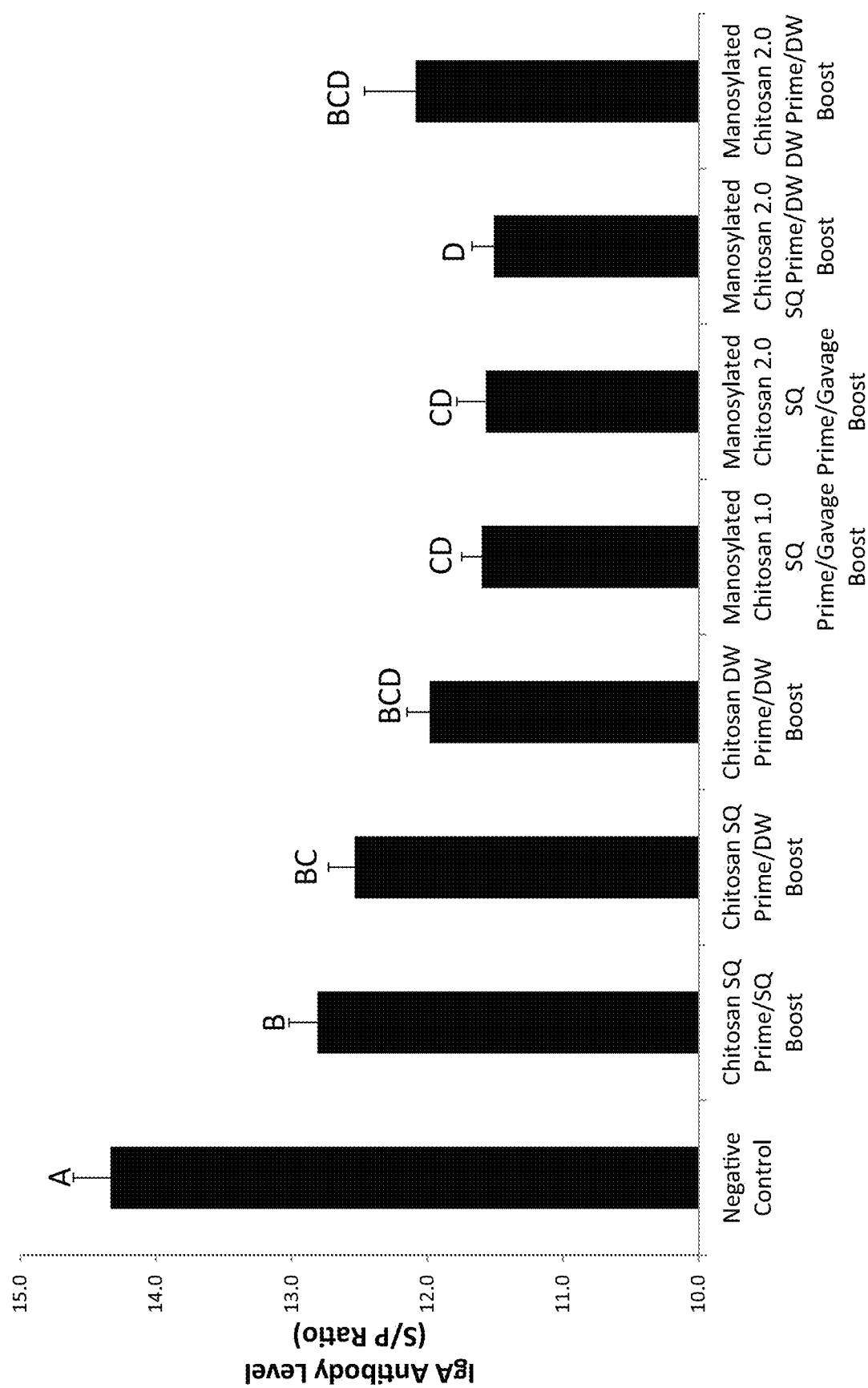
FIG. 8 is a graph showing the IgA antibody level against *Salmonella* at Day 22 following primary vaccination and boost (Day 12) with the indicated vaccine-adjuvant formulations via the indicated routes of administration as measured using a competitive ELISA. Different letters indicate significant differences ($p \leq 0.05$).

The carbohydrate-chitosan used herein is made as described more fully in the Examples below. Our method is based on Jayasree (Jayasree et al., 2011) using an open ring carbohydrate with an available carbonyl group that reacts with the amino group on chitosan to form a Schiff-base. This Schiff-base can be stabilized by reduction with sodium cyanoborohydride ($NaCNBH_4$). We have shown that the reduction was not necessary for immunopotentiation in FIG. 6 in which the reduced (Man-C V1) was compared to the non-reduced form (Man-C V2) of the chitosan. The non-reduced form produced the best IgA response, thus either form can be used. In addition, the non-reduced form of the mannosylated chitosan does not require the addition of a toxic chemical ($NaCNBH_4$). Briefly, the carbohydrate, suitably mannose (10 µM), is dissolved in 0.1M sodium acetate pH4.0 at 60° C. for 2 hours and chitosan (0.2-2%) is dissolved in 1.5% acetic acid. The dissolved mannose and the dissolved chitosan are then combined and incubated at room temperature to allow the amine group on the chitosan to react with the carbonyl on the sugar to produce a Schiff base. Reduction of the Schiff base is not necessary for the adjuvant to function and indeed the Examples show the non-reduced Schiff base is a better adjuvant (see FIG. 6). In other embodiments, the Schiff base may be reduced.

In another embodiment, chitosan and an antigen may be cross-linked using an aldehyde. In one aspect, a composition comprising 0.5% to 2% of an aldehyde cross-linked chitosan and an antigen. The final vaccine formulation suitably contains 0.5 to 1.5% chitosan. The adjuvant may contain 0.5% to 3% chitosan, suitably 0.5% to 2% chitosan, suitably 0.5% to 1.5% chitosan, suitably 0.5% to 1.2% chitosan. The final concentration of aldehyde in a vaccine composition is suitably less than 0.5%. The maximum concentration of aldehyde is based on the maximum level of residual aldehyde allowed in vaccines. A higher level of an aldehyde may be used for cross-linking the chitosan, but the final vaccine formulation suitably contains less than 0.5% aldehyde. In the Examples, formaldehyde was used as the aldehyde to cross-link the chitosan. Other aldehydes, such as formalin, glutaraldehyde, acetaldehyde, propionaldehyde, or butyraldehyde, may also be used. The aldehydes cross-link the chitosan amino groups with those on other chitosan molecules or on the antigens.

Methods of making a vaccine formulation comprising an aldehyde cross-linked chitosan and an antigen is also provided herein. The methods include dissolving chitosan in a solution of acetic acid. The carbohydrate-linked chitosan may also be used as the chitosan in this method. Suitably the acetic acid is used at 1.5% final concentration in water or 15 mL of acetic acid dissolved in 1 L of water. Suitably the amount of chitosan is between 0.5% and 2%, suitably between 0.5% and 1.5%. An antigen is added to the dissolved chitosan at the appropriate level. The amount and form of the antigens used in the vaccine formulations can be determined by those of skill in the art. Finally, the antigen and chitosan are combined with the aldehyde such that the final concentration of the aldehyde is between 0.02% and 0.5%. The aldehyde is capable of chemically cross-linking the chitosan to other chitosan molecules and the chitosan to the antigen. Tris-HCl can be added to quench free aldehydes. The Tris can be added to a final concentration of 0.5 g/L.

Either adjuvant composition disclosed herein may be combined with enhancing molecules including but not limited to saponin, toll-like receptors, the B subunit of a bacterial toxin, bacterial toxins, tetanus toxoid, CpG motifs, liposomes or monophosphoryl lipid A. Suitably the enhancing molecules act as further stimulators of the immune system and enhance the immune response generated after administration of the vaccine formulation to a subject.

The vaccine formulations provided herein comprise the chitosan-based adjuvants described herein and antigens. The antigens may be any antigens available to those of skill in the art. Antigens such as proteins, synthetic peptides, peptides conjugated to carriers, or microbes may be used in the vaccines. Microbes include bacteria, yeast, parasites, fungi, viruses, helminthes or other disease causing organisms. Microbes include live, dead, attenuated, recombinant, or inactivated organisms. Examples of microbes include, but are not limited to *Salmonella. Escherichia. Shigella, Bordeella, Clostridium, Mycplasma, Staphylococcus, Streptococcus, Bacillus, Influenza,* and *Eimeria*. Microbes may be inactivated or killed prior to use by treatment with heat, methanol or other fixatives such as formaldehyde or other aldehydes. The aldehydes can be quenched by subsequent addition of Tris-HC to a final concentration of 0.5 g/L. Suitable antigens may also include peptide antigens such as *Influenza* M2e, Hemaglutinin, Neuraminidase, or nuclear proteins; *Eimeria* TRAP or MPP; *Clostridium* sialidase, SagA, alpha-toxin, NetB toxin, or iron transport protein. Examples of other peptide antigens can be found at least in U.S. application Ser. Nos. 12/441,851; 12/740,631; 12/740,608; 13/574,504; and Ser. No. 13/702,827, all of which are incorporated herein by reference in their entireties. The chitosan based adjuvants may be used to increase the immune response to vaccines already available or to newly developed vaccines or autogenous vaccines.

There are two significant improvements to vaccination associated with this work. First, when modified chitosan is co-administered with inactive vaccine by the parenteral route, we see an immune response that is superior to the immune response observed with other adjuvants, such as alum, with a minimal injection-site reaction. Many adjuvants work by causing an inflammatory response at the site of injection or delaying absorption from the injection site, or both. One of the down sides to traditional adjuvants is that they often cause some reaction, soreness, and in some cases they cause persistent lesions that cause downgrading or trimming of meat-producing animals at slaughter. The modified chitosan may reduce these concerns associated other vaccine adjuvants. It is cheap to produce and easy to make into commercial vaccines.

In addition, robust immune responses are being generated when killed antigens are co-presented orally either by gavage or by inclusion in the drinking water. This is really important for domestic animals—especially for poultry, because handling for parenteral injection is very labor intensive and causes stress to the birds or other animals. With the exception of the hatchery, it is generally too expensive to use inactivated vaccines in poultry because of the administration cost. The ability to deliver the vaccine orally changes the way we are able to vaccinate animals. There are two main advantages of live (called modified live or attenuated vaccines) for mass administration. First, you can mass apply by drinking water or spray application. Second, these live vaccines also generate immunity in the local mucosa (respiratory tract and intestinal tract where most pathogens infect). As such, either killed or live vaccines can protect from disease, but the live vaccines are historically more effective at preventing actual infection, and therefore are preferred.

There are huge advantages to killed vaccines in that they can be produced quickly with very low risk of causing infection and disease, they cannot genetically change back into the disease-causing parent type, and they have much lower regulatory issues for these reasons. Also, there are a large and ever-growing number of orphan diseases which are not sufficiently common for a vaccine company to develop a regulated/licensed vaccine, and there are provisions in US law (and many other countries) for producing "autogenous" vaccines specifically made from the pathogen of interest, killed, and used on the source flocks (or animal or human populations). In developing countries orphan diseases occur that require vaccines that are not affordable or that are technically not possible to produce locally or quickly enough to deal with an outbreak. The adjuvants provided herein am affordable and technologically straightforward to produce. They can be readily combined with a killed or inactivated microbe to generate a vaccine.

Several potential applications for the technology described herein are available. The systemic response to killed vaccines can be improved by incorporation of the altered chitosan as an adjuvant for injection. We can prevent some diseases through oral administration of killed vaccines with this adjuvant platform. This adjuvant platform, when administered orally, may be targeted to stimulate systemic and/or mucosal responses—meaning that it has many of the advantages of live vaccines, but avoiding the issues of live vaccines described above.

The adjuvants and vaccine formulations described herein may be combined with other pharmaceutically acceptable carriers. A pharmaceutically acceptable carrier is any carrier suitable for in vivo administration. Examples of pharmaceutically acceptable carriers suitable for use in the compositions include, but are not limited to, water, butTered solutions, glucose solutions, oil-based or bacterial culture fluids. Additional components of the compositions may suitably include, for example, excipients such as stabilizers, preservatives, diluents, emusifiem and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be emulsified.

The compositions described herein may also be combined with other pharmaceutical compositions and these compositions may be administered in any order, at the same time or as part of a unitary composition. The two compositions may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

An effective amount or a therapeutically effective amount of the vaccine formulations as used herein means the amount of the composition that, when administered to a subject for enhancing the immune response of the subject to the targeted disease is capable of increasing the immune response, such as the cell-mediated or antibody mediated immune response to limit the morbidity or mortality associated with infection or exposure to the targeted disease. Suitably, the immune response is enhanced to a level such that administration is sufficient to effect a treatment or block disease related morbidity or mortality. The therapeutically effective amount will vary depending on the vaccine, formulation or composition, the disease and its severity and the age, weight, physical condition and responsiveness of the subject. For example the level of antibody produced in response to vaccination may be increased by two fold, three fold, four fold or more by inclusion of the adjuvant described herein as compared to administration of the same antigen without an adjuvant or with alum as an adjuvant. The increased immune response may be an IgA response, or an IgG response. The adjuvant may also lead to a reduction in the morbidity or mortality associated with subsequent infection. As shown in the Examples, use of the adjuvants described herein in combination with an antigen may lead to a reduction in the rate of subsequent infection or the severity of subsequent infection with the microbe to which the antigen elicits an immune response as compared to vaccination with the antigen alone or vaccination with the antigen and a distinct adjuvant. The severity of the infection may be measured by the ability of a microorganism to invade tissues beyond the site of introduction, replicate and/or persist within the organism over time, or cause morbidity or mortality. The vaccinated animals may be subsequently infected with a pathogen. In such cases, the growth of the pathogen in the subject after challenge is reduced by at least 1 $\log_{10}$, 2 $\log_{10}$ or even 3 $\log_{10}$ in subjects administered the vaccine as compared to subjects administered a control.

The compositions described herein may be administered by any means known to those skilled in the art, including, but not limited to, oral, intranasal, intraperitoneal, parenteral, intravenous, intramuscular, subcutaneous, nasopharyngeal, or transmucosal absorption. Thus the compounds may be formulated as an ingestable, sprayable or injectable formulation. For example, oral administration may entail addition to the drinking water, spraying on food, spraying on the animals (such as chickens or turkeys that will ingest the vaccine in the spray when they preen their feathers). The subjects may be mammals, including humans, cows, pigs, cats, dogs or other domesticated animals or non-mammals such as poultry, i.e., chickens or turkeys.

It will be appreciated that the specific dosage administered and timing of administration (i.e. primary vaccination and boost) in any given case will be adjusted in accordance with the formulation being administered, the disease being targeted, the risk of exposure, the condition of the subject, and other relevant medical factors that may modify the response of the subject or feasibility of providing the formulation to the subject. For example, the specific dose for a subject depends on type of subject, age, body weight, general state of health, diet, the timing and mode of administration, the rate of excretion, medicaments used in combination and the severity of the particular disorder to which the vaccine is targeted. The initial vaccination and the boost may be administered by different means. For example, an initial vaccination via a subcutaneous route can be boosted by inclusion of the adjuvant-antigen complex in the drinking water or food. The percentage of chitosan in the vaccine formulations is generally between 0.2 and 2%, suitably 0.5-1.5%. The total amount of chitosan administered may be from less than mg per vaccination to 100 mg, suitably, 2, 4, 5, 6, 8, 10, 12, 14, 16, 18, 20, 25, 50, 75 or 100 mg of chitosan. In the Examples, 2-5 mg chitosan was used per dose. When combined with a microbial antigen, the microbe may be included at between $1\times10^6$ to $1\times10^9$ microbes per dose. In the Examples, $1\times10^7$ to $1\times10^8$ microbes were used per dose. An antigen may be included at 10 µg to 10 mg per dose. In the Examples, 100 µg per dose was used.

The following examples are meant only to be illustrative and are not meant as limitations on the scope of the invention or of the appended claims. All references cited herein are hereby incorporated by reference in their entireties.

EXAMPLES

Example I: Immune Response to β-Galactosidase Following Primary Vaccination and Boost Our first experiment to test the chitosan-protein cross-linked with formaldehyde vaccine used the classical protein β-galactosidase (β-Gal) as a model protein. Turkey poults were vaccinated with β-Gal, as described in Table I below, with six treatment groups and one control. Poults were vaccinated with saline or β-Gal 100 µg (0.25 ml) in either saline, 15% alum, 1% chitosan cross-linked (3 groups) with formaldehyde (Form), or 1.5% chitosan not cross-linked with formaldehyde by parenteral subcutaneous (sq) injection at day-of-hatch. All groups were boosted with the same formula sq at days 14 and 25 except two of the 1% chitosan groups, one boosted both days with 1% chitosan-β-Gal by oral gavage and one boosted by spray with 1% chitosan-β-Gal (2 mL).

Figure 1:
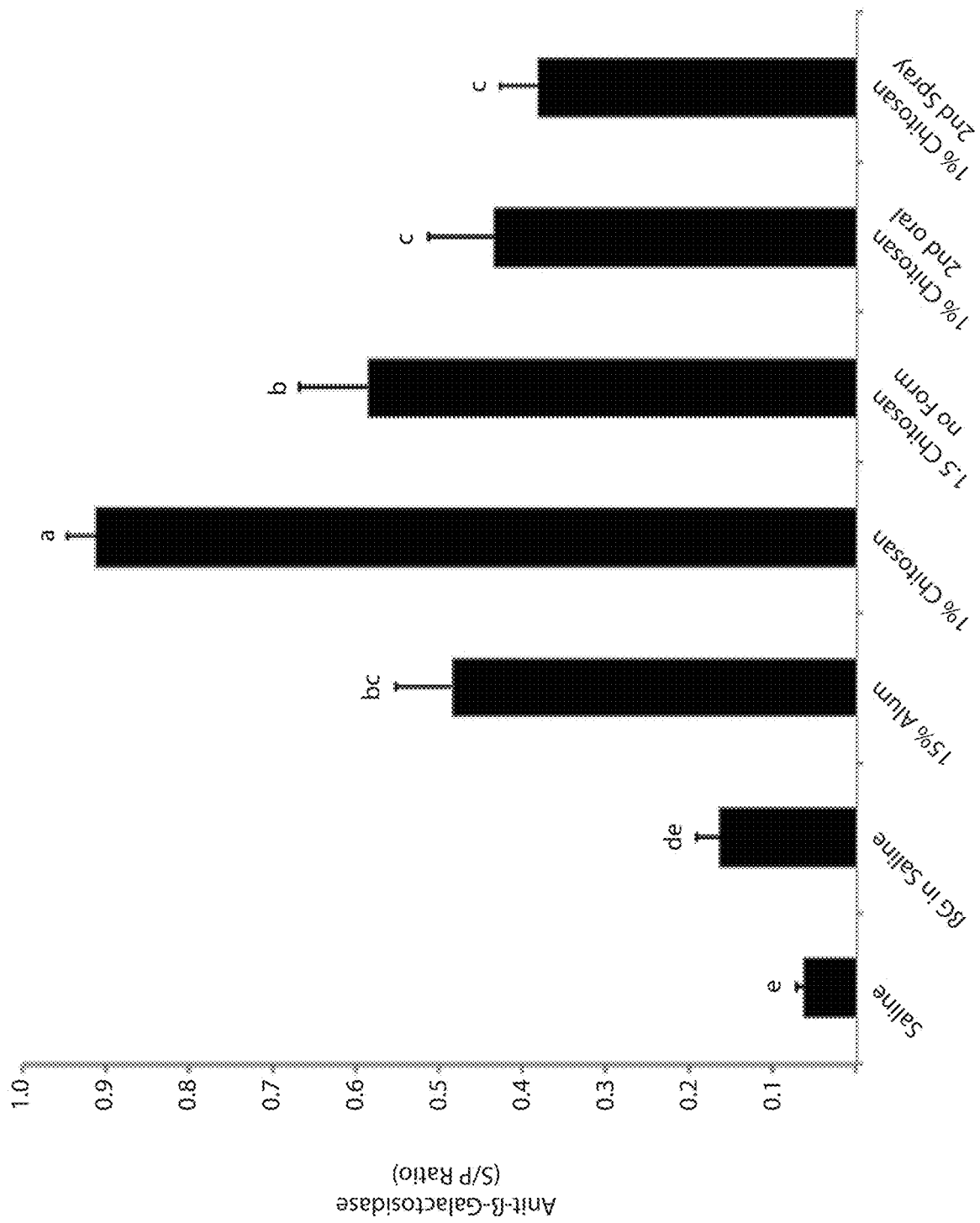
FIG. 1 is a graph showing the anti-β-galactosidase IgG antibody response in turkeys following primary vaccination and boost with the indicated vaccine-adjuvant formulations. Different letters indicate significant differences ($p \leq 0.05$).

The immune response to the β-Galactosidase was determined using serum in an ELISA for β-galactosidase and the results are shown in FIG. 1. Levels of the immune response are reported as sample to positive control ratios of absorbance in an indirect ELISA. Higher S/P ratios indicate higher anti-β-galactosidase antibody titers. There was very little cross-reactivity in the ELISA using serum from turkeys vaccinated with saline and only a modest numerical increase when vaccinated with β-Gal in saline. A common commercial adjuvant used currently is 15% alum and there was a good immune response when this was used. Using our chitosan-immunostimulated and formaldehyde cross-linked vaccine system (labeled as 1% chitosan) there was a significant increase in the immune response to the model antigen, β-Gal. Using chitosan alone even at a higher concentration of 1.5% there was a significantly lower immune response. In addition, when the antigen was boosted with 1% chitosan-formaldehyde treated adjuvant by spray or oral treatment, there was a response comparable to the standard adjuvant, 15% alum, administered subcutaneously.

TABLE 1

Treatment Groups

| Group | Immunogen | Primary Day-of-hatch VX (100 µg/0.25 ml) | Boost at 14 days after hatch |
|---|---|---|---|
| Saline | None | SQ | SQ (100 µg/0.5 ml) |
| βG in Saline | β-Galactosidase | SQ | SQ (100 µg/0.5 ml) |
| 15% Alum | β-Galactosidase | SQ | SQ (100 µg/0.5 ml) |
| 1% Chitosan | β-Galactosidase | SQ | SQ (100 µg/0.5 ml) |
| 1.5% Chitosan no Form | β-Galactosidase | SQ | SQ (100 µg/0.5 ml) |
| 1% Chitosan $2^{nd}$ oral | β-Galactosidase | SQ | Oral gavage (100 µg/0.5 ml) |
| 1% Chitosan $2^{nd}$ Spray | β-Galactosidase | SQ | Spray (100 µg/ml) atomized spray of 50 ml per 20 birds in a 20 sq. ft. room |

Example II: Immune Response to *Clostridium* Following Vaccination with Various Adjuvants A similar experiment to the one described above was carried out by administering $4\times10_8$ cfu/ml *Clostridium septicum* bacterin (CS) in either alum or formalin-cross-linked chitosan so that the final dose per bird is $1\times10^8$ cfu/bird today-of-hatch turkey poults subcutaneously (in 0.25 mL) either alone or in combination with 12% alum or 0.5% formalin-cross-linked-chitosan. All birds were boosted at day 14 with the same vaccine by the same route. Levels of the resulting immune response were measured by an indirect ELISA assay and reported as sample to positive control (S/P) ratio of absorbance. Higher S/P ratios are indicative of higher anti-CS antibodies.

Figure 2:
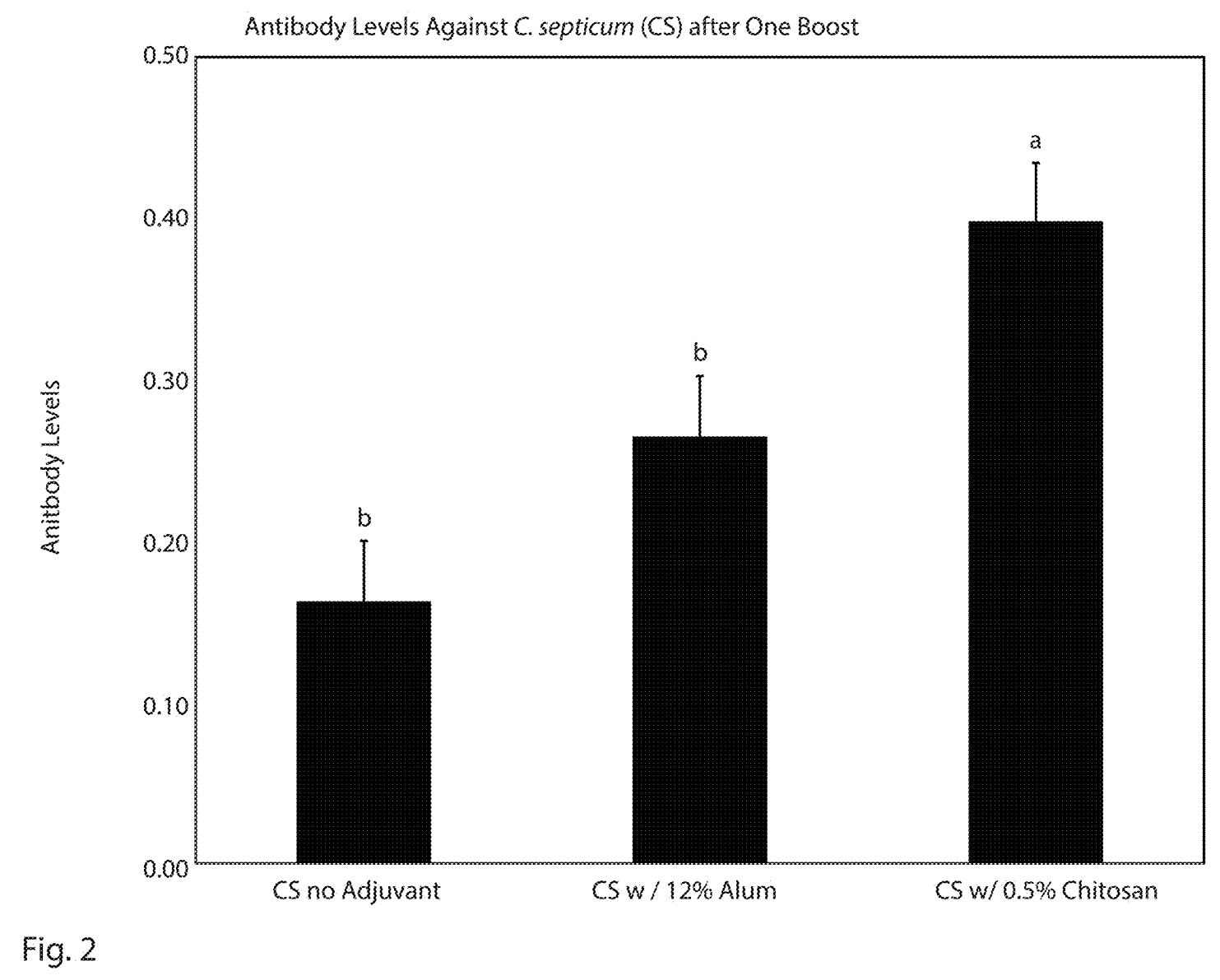

Birds receiving vaccine without adjuvant resulted in an ELISA-detectable antibody response with an S/P ratio of 0.16 as shown in FIG. 2. This antibody level was not statistically different from that of the CS adjuvanted with alum. After one boost (14 days after primary vaccination), poults vaccinated with the CS bacterin adjuvanted with 0.5% formalin-cross-linked-chitosan showed IgG levels that resulted in S/P ratios approximately double that of the CS bacterin without adjuvant, 0.4 and 0.16 respectively. The CS bacterin with aluminum hydroxide adjuvant induced IgG levels that were approximately 30% lower than IgG levels induced by CS with chitosan compared by S/P ratios, 0.27 and 0.4, respectively. (See FIG. 2). Importantly, injection site lesions are less pronounced at 72 hours (or later) due to chitosan administration whereas alum always produces local inflammation and granulomas, often progressing to encapsulated scar tissue.

Example III: Avian Influenza Vaccination Experiments

Avian influenza (AI) is a significant public health concern and serious economic threat to the commercial poultry industry worldwide. Our previous data suggest that *Salmonella*-vectored vaccines expressing M2e in association with CD154 are effective against AI. New constructs using *Bacillus subtilis* as the vector and M2e epitopes with immunostimulatory molecules were tested. M2e specific serum IgG and mucosal IgA antibody levels were determined by ELISA on days 11, 15 and 21 post hatch. On day-of-hatch chicks were vaccinated by either oral gavage or subcutaneous injection with either *Bacillus* Wild Type (BSBB), *Bacillus* vectored avian influenza vaccine (BSAI) as a live vaccine, BSAI after formalin inactivation, BSAI after formalin inactivation, lyophilization and reconstitution with saline or BSAI after formalin inactivation and cross-linked with 1% chitosan. Each vaccine was administered at $10^6$ cfu/chick in 0.25 ml or 0.25 ml saline. On day 10 post-hatch chicks in two groups (BSAI live, BSAI inactivated and lyophilized) were given a booster vaccination of the same treatment they received at day 0 and all other groups did not receive the $2^{nd}$ vaccine dose.

Serum IgG and mucosal IgA samples were then obtained from birds in all groups on days 11, 15 and 21 post hatch and used in an antibody capture ELISA. Plates were coated with M2e conjugated to BSA (10 µg/ml), blocked, incubated with serum from each of the treatment groups diluted 1:50 in 2% FBS/PBS, followed by incubation with a HRP-conjugated secondary antibody diluted 1:7,500, and developed using TMB substrate. The results are presented as mean S/P ratios (sample mean−negative control mean)/(positive control mean−negative control mean)±SEM (n=20).

When compared with the *Bacillus* backbone control (BSBB), there were significant increases in M2e specific IgG antibody responses in each vaccinated group at each time point tested. However, there were no differences observed within each time point between any of the six vaccinated groups in increased IgG antibody response (See FIG. 3A). The real difference in immune response is apparent when looking at the mucosal IgA specific antibody response (See FIG. 3B). BSAI+1% chitosan showed a marked increase in specific IgA antibody response when compared to control or the additional five treatment groups receiving vaccination at all three time points sampled.

To summarize, in experiments using cross-linked chitosan we have demonstrated above that this modification of chitosan is a better adjuvant than aluminum hydroxide through both parenteral and oral routes (FIGS. 1 and 2). Chitosan treated with formaldehyde as a cross-linker was shown to be more effective than chitosan without formaldehyde (FIG. 1). When used orally, chitosan enhanced the production of IgA (FIG. 3B) preferentially over IgG (FIG. 3A).

Example IV: Enhancement of Chitosan Adjuvant

The adjuvant was further enhanced through a series of experiments designed to improve the chitosan-based adjuvant by addition of potential enhancing molecules or alternative delivery strategies. Immunostimulatory compounds can potentially improve responses when used with adjuvants and several have been investigated previously; see reviews (Guy, 2007; Mutwiri et al., 2011). Potential adjuvants include saponins, bacterial components, compounds that interact with the innate immune system such as Toll-like receptors, nucleic acids such as the CpG motif, viruses, emulsions including liposomes, or a combination of any of these components. Some of the more promising immunostimulatory molecules that interact with the innate immune system are Tetanus toxoid (TT), heat-labile enterotoxin B subunit (LTB), and Cholera toxin B subunit (CTB). Other compounds shown to enhance the immune system empirically through innate chemical properties include saponin and monophosphoryl lipid A (MPLA). Using mannose or other sugars to target binding to macrophage receptors may enhance immune function. Combinations of different adjuvants may act synergistically such as with IL-12 or other cytokines to stimulate the immune response.

Figures 3, 3B:
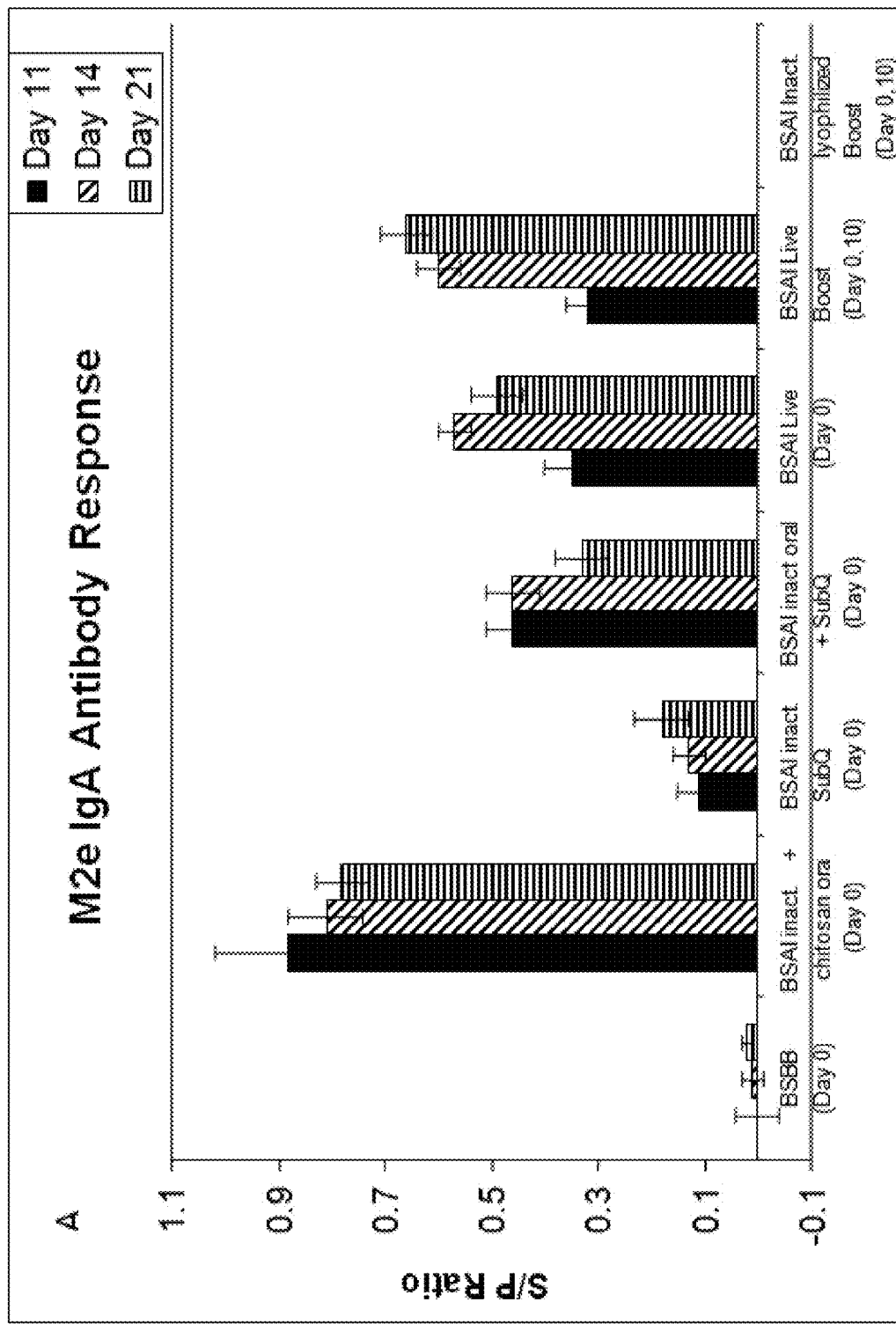
FIG. 3 is a set of graphs showing the IgG (FIG. 3A) and IgA (FIG. 3B) antibody response in chickens at various time points after vaccination and boost with the indicated *Bacillus*-vectored avian influenza vaccine-adjuvant formulations.
Figure 4:
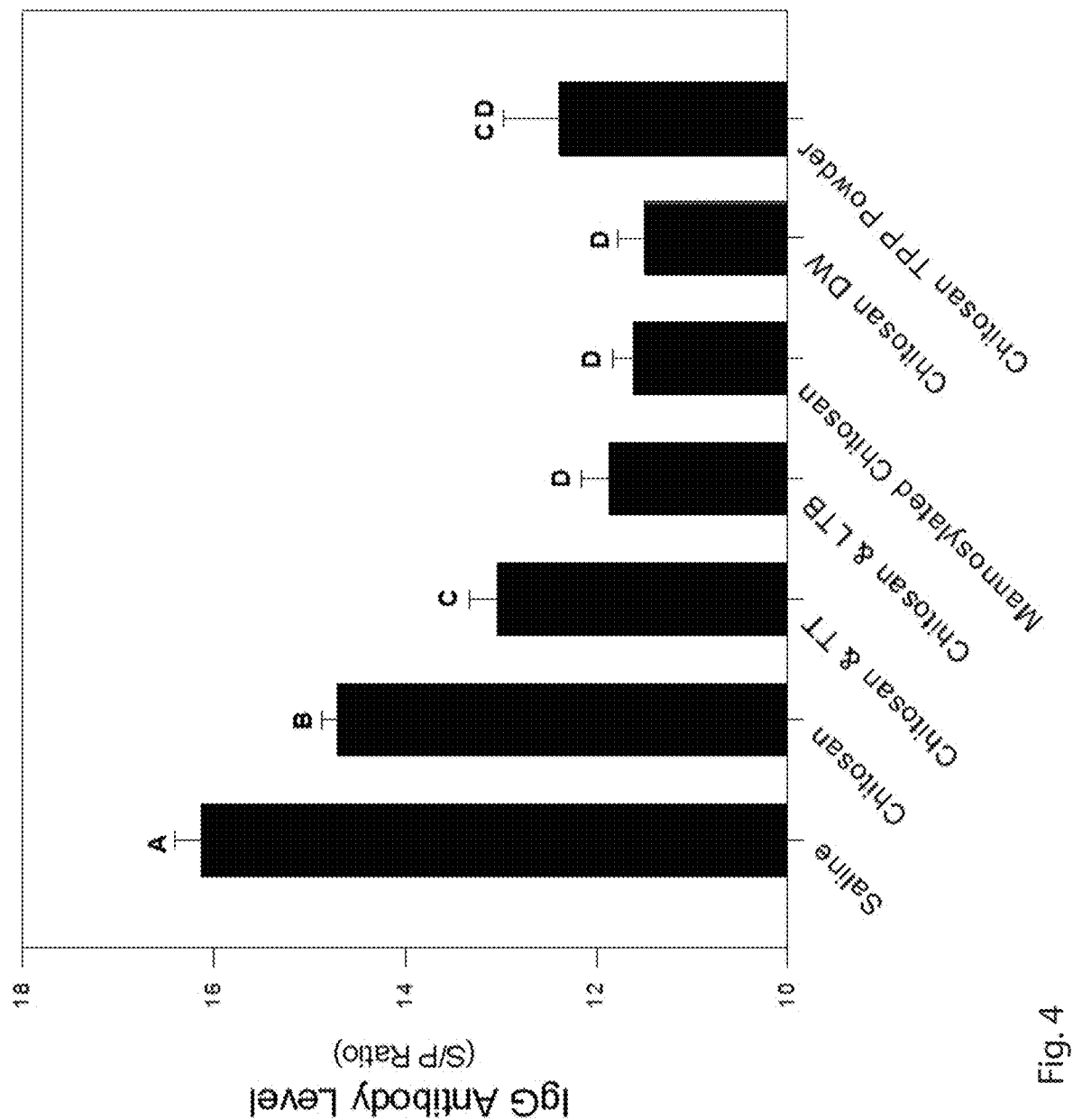
FIG. 4 is a graph showing the IgG antibody levels against *Salmonella* following primary vaccination and boost with the indicated vaccine-adjuvant formulations measured using a competitive ELISA. Different letters indicate significant differences ($p \leq 0.05$).
Figure 5:
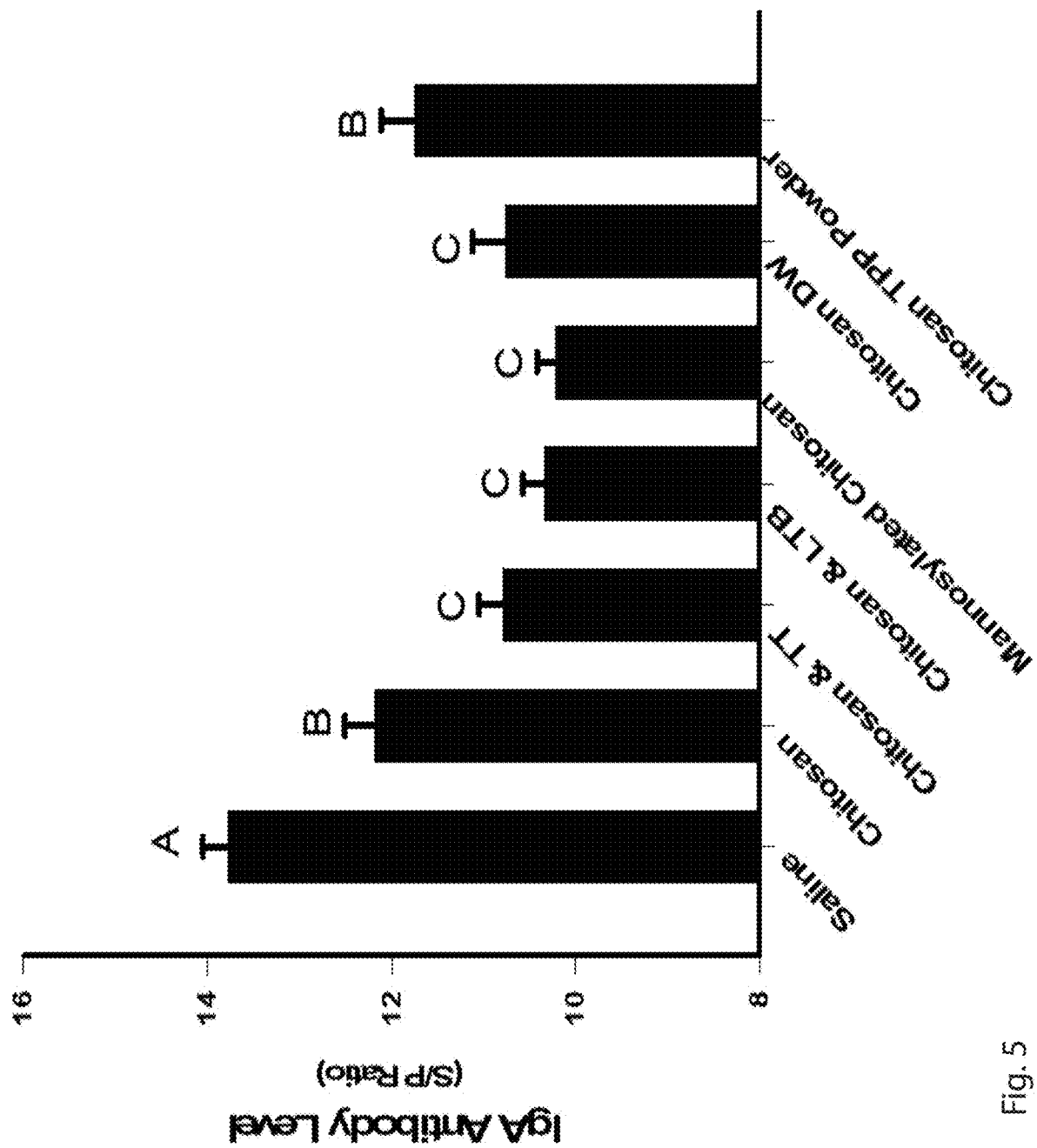
FIG. 5 is a graph showing the IgA antibody levels against *Salmonella* following primary vaccination and boost with the indicated vaccine-adjuvant formulations measured using a competitive ELISA. Different letters indicate significant differences ($p \leq 0.05$).

The first experiment to improve the adjuvant compared the formaldehyde-cross-linked chitosan adjuvant, which consists of an antigen of interest cross-linked with 0.5% chitosan, using formaldehyde to generate the data shown in FIGS. 1-3 above. This adjuvant system was then used as the control or baseline for selection of the best combinations of selected candidate immune enhancing molecules. The test immunogen was a *Salmonella enteritidis* (SE) bacterin grown to 10 cfu/ml and inactivated with formaldehyde. To determine whether the cross-linked chitosan adjuvant could be further improved, the test immunogen (*Salmonella* bacterin with chitosan was $4\times10^7$ cfu/ml with a final dos of $1\times10^7$ cfu per bird) was mixed in a 2:1 ratio with cross-linked chitosan alone or enhanced with tetanus toxoid (TT), heat-labile enterotoxin B subunit (LTB), or mannosylated chitosan and administered in either the drinking water or feed. The results are presented in FIG. 4.

TT may be a potential immune enhancing molecule and has been used extensively in vaccine development. The heat-labile enterotoxin from *E. coli* has been shown to be a powerful immunostimmulatory molecule but is very toxic and is, therefore, not suitable as an adjuvant. The heat-labile enterotoxin consists of two subunits, a central core LTA and five subunits of LTB (da Hora et al., 2011). The LTB subunit retains the immune adjuvant properties and yet is non-toxic. Therefore, this is a safe potential adjuvant component. Mannose and some other carbohydrates (such as galactose and fucose) are ligands for receptors that activate macrophages. The mannosylated chitosan was prepared by a method similar to that described previously by Yalpani and Hall (1980 and 1985) and Jayasree et al., (2011) without the addition of the zinc. Briefly, two molar equivalents of mannose in one volume of 0.1 M sodium acetate were heated at 60° C. for two hours. The solution was then added to two volumes of one molar equivalent of 2% chitosan in 0.15% acetic acid and allowed to react for 10 min at room temperature to produce 1.5% mannosylated chitosan. The SE bacterin was then added to 1.5% mannosylated chitosan in a two to one ratio. The Schiff-bases formed were then reduced with sodium cyanoborohydrate ($NaCNBH_4$).

In addition, to the immunopotentiating molecules, different delivery systems were also investigated as noted above. The typical drinking water delivery system used in the poultry industry dilutes the drug or chemical one part to 128 parts of water. The original chitosan formula used in FIGS. 1-3 was diluted 1:128 in the drinking water as a potential delivery system. The last test group was 0.5% chitosan cross-linked with formaldehyde with the SE bacterin (original chitosan formula) encapsulated by drop wise addition to tripolyphosphate (TPP) then dried and ground to a powder for addition to the feed at a rate of 0.5% (wt/wt).

Day-of-hatch broiler chicks were primed with 0.25 ml of the indicated preparations subcutaneously as outlined above. These groups were primed the same as the chitosan only group. Chicks were boosted by oral gavage at 12 days of age except for the drinking water and TPP groups which were boosted in water at 1:128 or in the feed at 0.5% (wt/wt) for 8 hours, respectively. Antibody levels on day 22 in serum (IgG) and ileal mucosal (IgA) were determined with a competitive ELISA kit (IDEXX). Decreased absorbance levels or sample to control ratios indicate higher levels of antibodies that recognize the SE flagellin coated plates.

Figure 9:
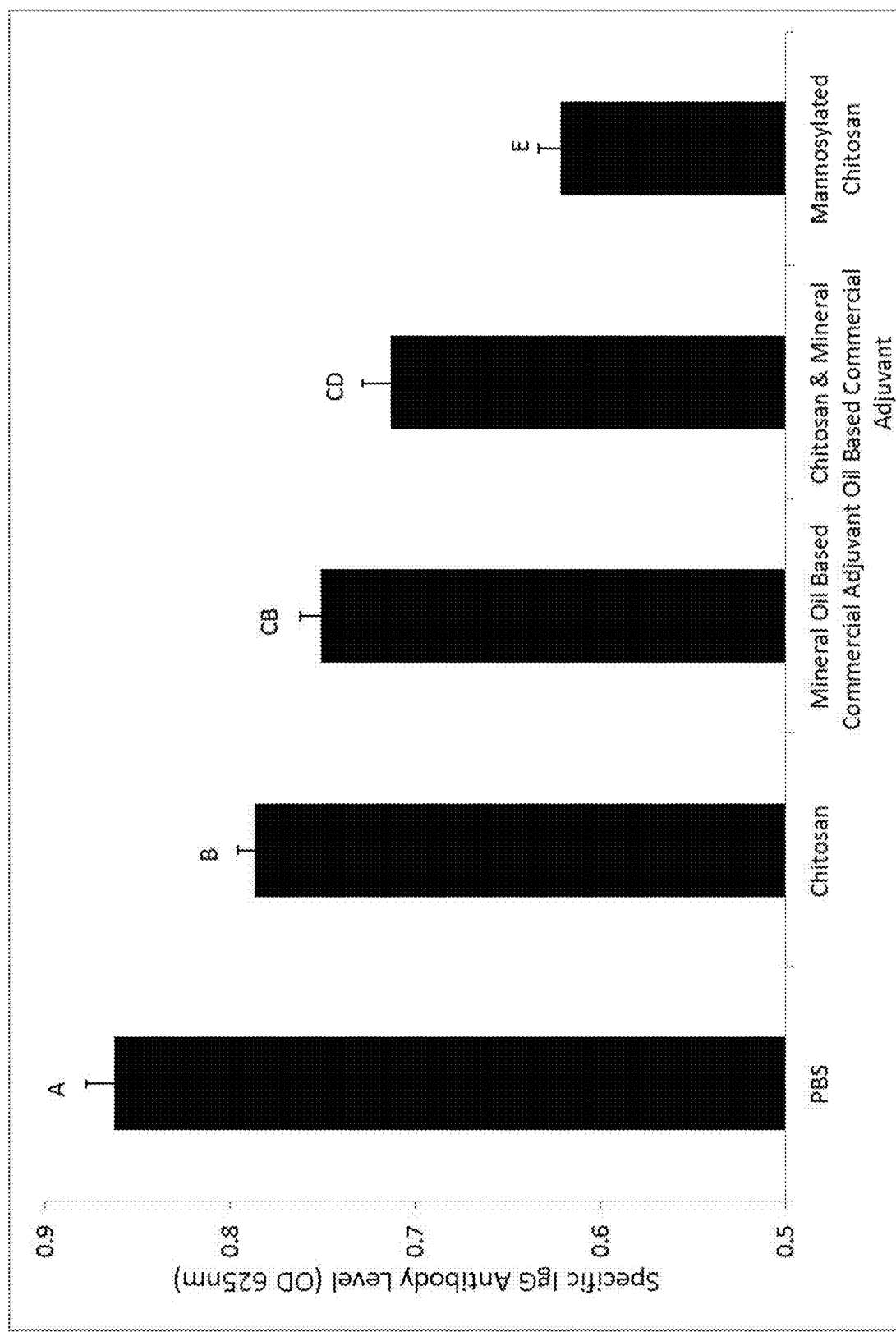
FIG. 9 is a graph showing the gG immune response to *Salmonella* after vaccination of chicks with the indicated vaccine-adjuvant formulations as measured by a competitive ELISA. Different letters indicate significant differences ($p \leq 0.05$).
Figure 10:
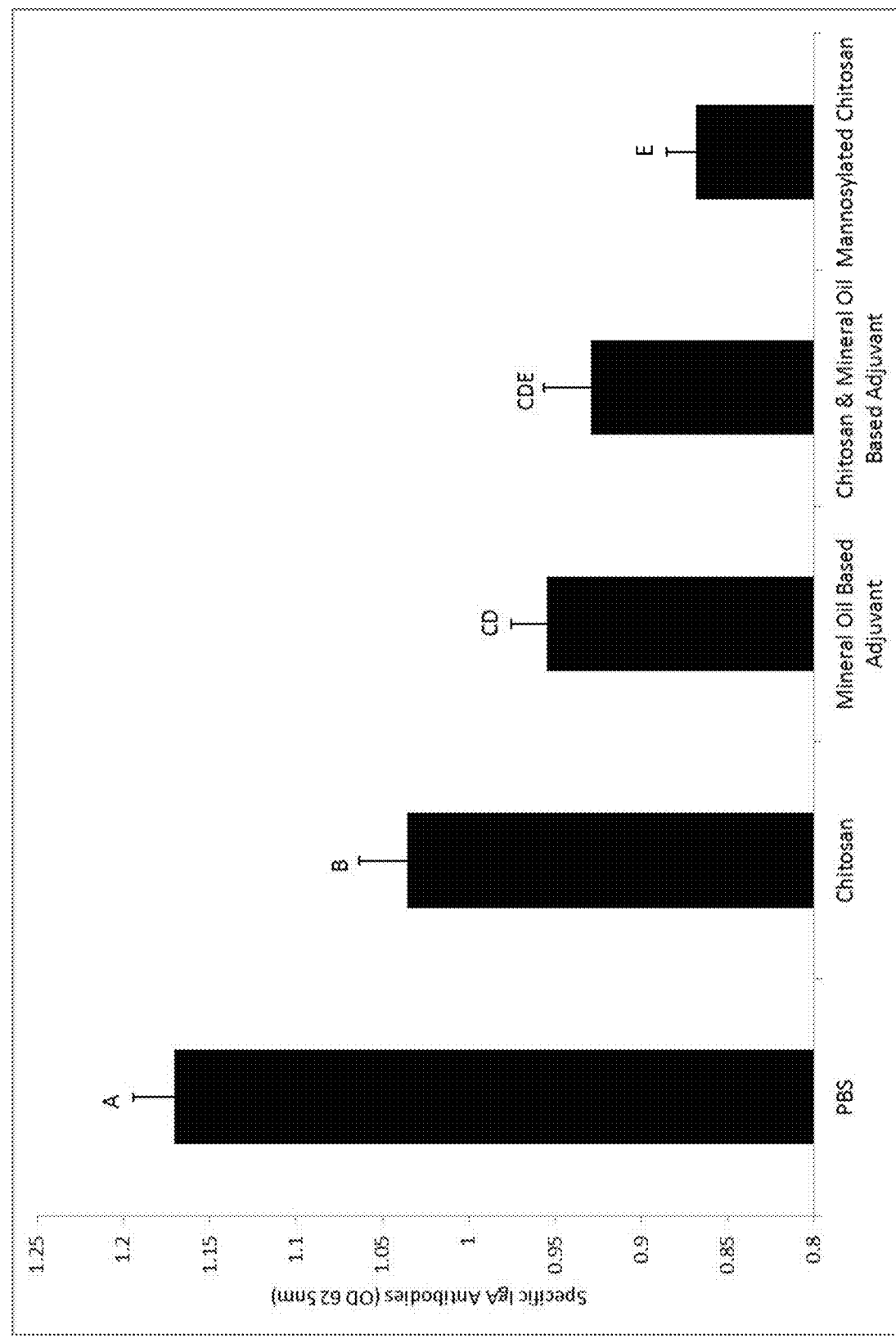
FIG. 10 is a graph showing the IgA immune response to *Salmonella* after vaccination of chicks with the indicated vaccine-adjuvant formulations as measured by competitive ELISA. Different letters indicate significant differences ($p \leq 0.05$).

As noted in FIGS. 1 and 2 above the chitosan adjuvant was superior to alum in producing a robust immune response. Here each of the chitosan based adjuvants was able to produce a robust response to the SE bacterin, with significantly higher levels of both IgG and IgA as compared to chitosan alone administered subcutaneously (FIGS. 4 and 5, respectively). The TT and dry powder TPP groups had a significantly higher immune response than the sq primed with sq boost chitosan adjuvant (FIGS. 4 and 5). The other three groups, chitosan with LTB, mannosylated chitosan, and chitosan boost in the drinking water, were consistently superior in antibody production as compared to chitosan alone administered subcutaneously (FIGS. 4 and 5).

In the next set of experiments, the three best groups from the previous experiment (LIB, chitosan boost in DW, and reduced mannosylated chitosan) were repeated along with the negative control (saline) and the benchmark control of 0.5% formaldehyde-cross-linked-chitosan administered sq for primary and boost vaccinations, which was previously shown to be superior to alum. In this experiment, we added three new treatment groups using the benchmark control of 0.5% formaldehyde-cross-linked-chitosan immunopotentiated with either Cholera toxin B subunit (CTB), Lipid A from *Salmonella* (MPLA), or saponin. Also added in this experiment was another treatment group that was the similar to the mannosylated chitosan treatment group, which was shown to be an excellent adjuvant in the previous experiment (Mannosylated chitosan version 1, Man-C V1), but this group was not reduced with $NaCNBH_4$ (Man-C V2).

The SE flagellin competitive ELISA again showed that the birds vaccinated subcutaneously with 0.5% chitosan (C) for both the primary and boost had higher levels of immunoglobulins in the serum (FIG. 6A). The birds vaccinated with 0.5% chitosan with CTB (C+CTB), Man-C V2 and Chitosan with saponin (C+saponin) gave the best IgG response (FIG. 6A). The Man-C V2 gave numerically the best IgA response (FIG. 6B). All three of these treatment groups were significantly different from the benchmark group (0.5% chitosan vaccinated sq for both the primary and boost) (FIG. 6).

In addition, the birds were challenged at day 19 with live *Salmonella* at $5\times10^7$ cfu/chick. Three days post-challenge the birds were cultured for *Salmonella* in the cecal tonsil (CT) and liver/spleen (US). Chitosan with CTB, both versions of mannosylated chitosan, chitosan in the drinking water boost, and chitosan plus saponin significantly decreased *Salmonella* to below detectable limits in the liver/spleen (US) when compared to the negative (saline vaccinated) control (FIG. 7; $p\leq0.05$). In the intestine (CT), the levels of *Salmonella* were significantly reduced using either of the two versions of mannosylated chitosan and in the group boosted with 0.5% chitosan diluted 1:128 in the drinking water. The significant decrease in the mannosylated chitosan groups indicate that the direct targeting of the macrophage with a ligand for the mannose receptor increases the effectiveness of the chitosan adjuvant. Also, very important is that the non-reduced Schiff-base formulation of the mannosylated chitosan was just as effective as the $NaCNBH_4$ reduced mannosylated chitosan which did not have the addition of a potentially harmful chemical. Another major surprise was that the 1:128 diluted 0.5% chitosan in the drinking water that was used for the boost gave superior results in decreasing colonization of *Salmonella* compared to parenteral vaccination only (FIG. 7).

Example V: Route of Administration for Vaccination

The best route and adjuvant combination for vaccination was investigated. Day-of-hatch chicks were administered 0.25 mL of either saline or the vaccine with the respective adjuvant mixture as indicated in FIG. 8. The adjuvants compared include the formaldehyde-cross-linked chitosan, the reduced mannosylated chitosan (Man C V1), the non-reduced mannosylated chitosan (Man C V2), and each adjuvant was combined with antigen and administered at day-of-hatch either subcutaneously or in the drinking water. Birds were boosted with a second administration of the same adjuvant-antigen combination either subcutaneously, in the drinking water or via oral gavage. The groups that were vaccinated in the drinking water (DW) were diluted 1:128 in the water. Those boosted by oral gavage were given 0.25 ml. Mucosal IgA response was measured using a competitive SE flagellin ELISA assay (IDEXX) as described above. Although the last five treatment groups in FIG. 8 were not significantly different, the numerically lowest group was the mannosylated chitosan V2 delivered sq in the primary vaccination and a 1:128 dilution in DW for the boost. This group had significantly higher levels of IgA in the ileum compared to 0.5% chitosan with sq primary vaccination and either sq or DW boost. No significant differences were observed between the reduced and non-reduced forms of the mannosylated chitosan or when the boost was given via the drinking water or oral gavage.

Example VI: Comparison to a Mineral Oil Based Adjuvant

The mannosylated chitosan was then compared to and combined with a commercially available mineral oil based adjuvant. *Salmonella enteritidis* (SE) bacterin grown to $10^8$ cfu/ml and inactivated with formaldehyde was used as the antigen. The *Salmonella* bacterin was mixed with chitosan, mannosylated chitosan, the mineral oil adjuvant, a combination of chitosan and the mineral oil adjuvant or PBS at $4\times10^7$ cfu/ml with a final dose of $1\times10^7$ cfu per bird in a 2:1 ratio. Day-of-hatch broiler chicks were primed with 0.25 ml of the indicated preparations subcutaneously as outlined above. Chicks were boosted by oral gavage at 12 days of age. Antibody levels on day 22 in serum (IgG) and ileal mucosal (IgA) were determined with a competitive ELISA kit (IDEXX) and results are shown in FIGS. 9 and 10, respectively. Decreased absorbance levels of sample to control ratios indicate higher levels of antibodies that recognize the SE flagellin coated plates. The mannosylated chitosan vaccination and boost protocol produced significantly increased IgG and IgA levels as compared to each of the other groups.

Example VII: IgG Response after a Single Administration

Figure 11:
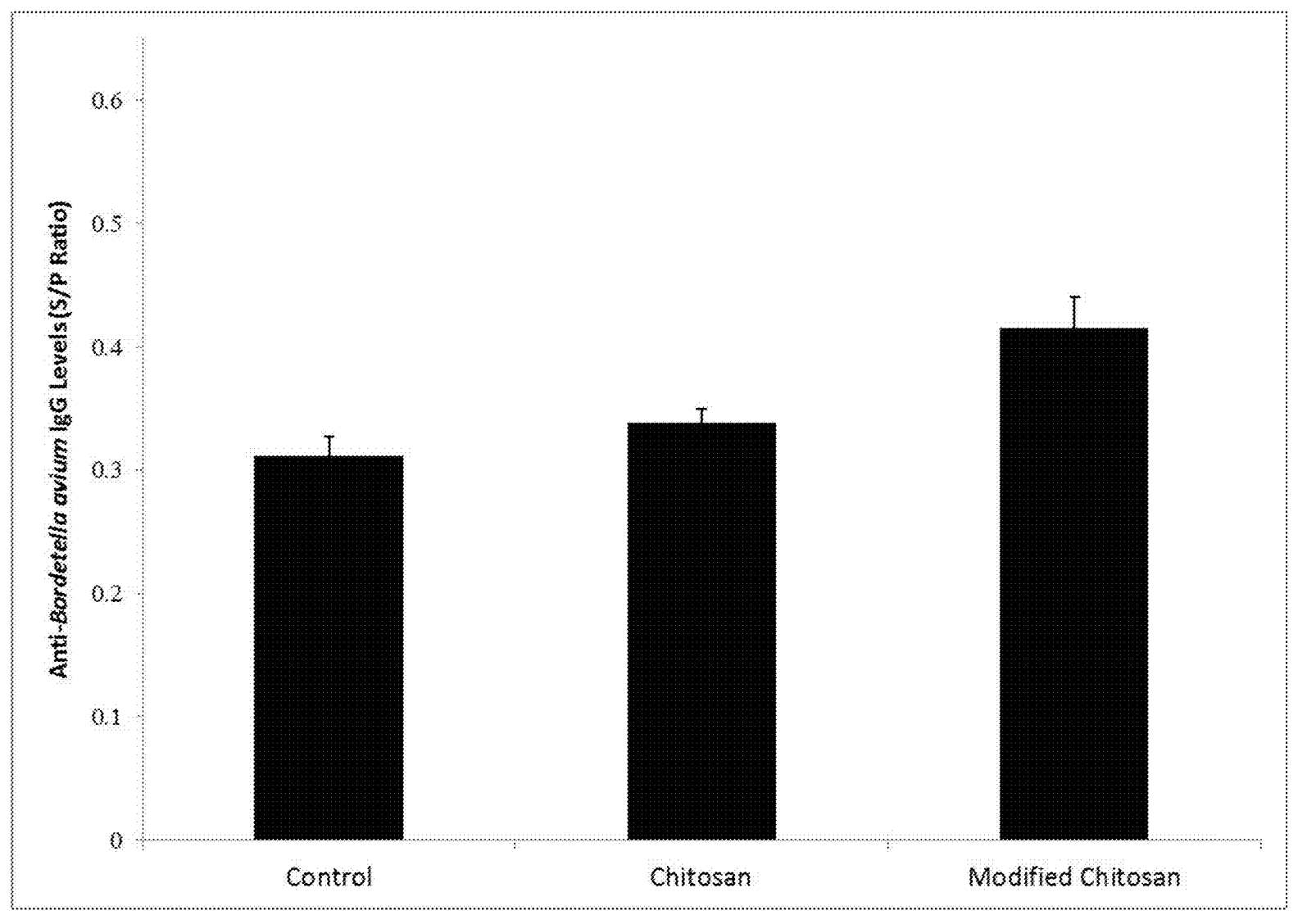

To investigate the IgG immune response after a single parenteral vaccination, day-of-hatch chicks were vaccinated subcutaneously with $2.5\times10^8$ cfu/poult *Bordetella avium* bacterin combined with saline, normal chitosan or mannosylated chitosan. Serum was collected at day 14 and the *Bordetella* specific IgG was measured by ELISA. The results are shown in FIG. 11 and show the sample to positive control ratios of absorbance for the indicated treatments. Higher levels of absorbance are indicative of increased specific IgG. The mannosylated chitosan combined with the *Bordetella* antigen produced the highest levels of IgG.

Example VIII: IgG Response after Boost in the Drinking Water

Figure 12:
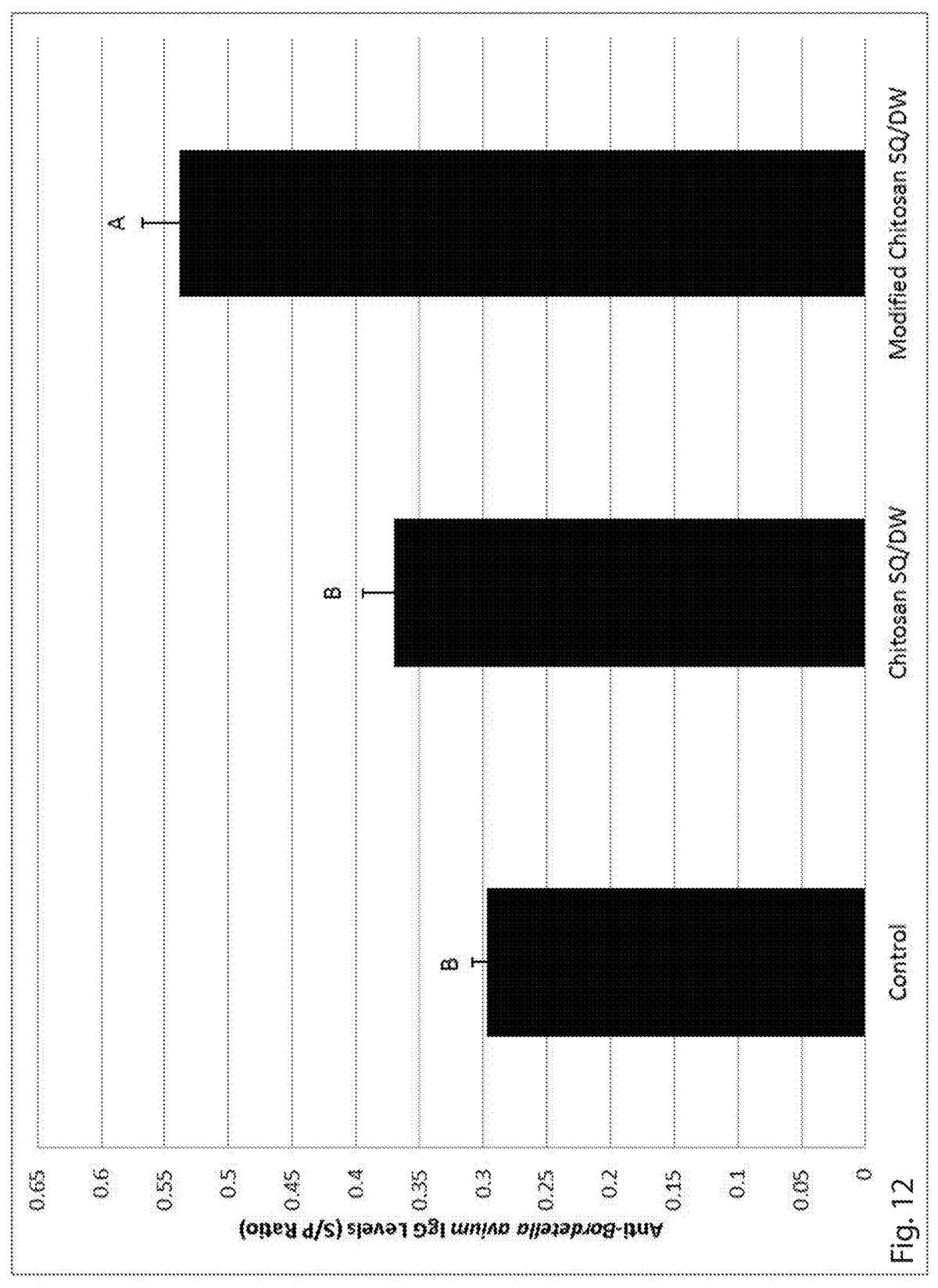

To investigate the IgG immune response after administration of *Bordetella avium* bacterin subcutaneously followed by a drinking water boost at day 14. Day-of-hatch chicks were vaccinated subcutaneously with $2.5\times10^8$ cfu/poult *Bordetella avium* bacterin combined with saline, normal chitosan or mannosylated chitosan. At day 14, $7.8\times106$ cfu/mL *Bordetella avium* bacterin was included in the drinking water as a boost to vaccination. At day 21, 7 days post-boost serm was collected and the specific IgG response was measured by ELISA. The results are shown in FIG. 12 and show the sample to positive control ratios of absorbance for the indicated treatments. Higher levels of absorbance are indicative of increased specific IgG. The mannosylated chitosan combined with the *Bordetella* antigen produced significantly higher levels of IgG as compared to the control or unmodified chitosan.

Methods for Adjuvant Preparation:
Preparation of Chitosan-Protein Cross-Linked with Formaldehyde Vaccine:

The final product of chitosan without mannose can range from a minimum final concentration of 0.5% chitosan and maximal final concentration of 2% chitosan in the vaccine formulation. Chitosan is dissolved in a solution containing 15 ml of glacial acetic acid per L deionized water at the appropriate concentration (1.5% acetic acid in water). Typically for broth cultures 2 volumes of culture are mixed with one volume of 1.5% chitosan (0.5% chitosan in the final vaccine formulation). Other antigens are diluted as minimal as possible giving a final concentration of up to 1.5% chitosan. The formaldehyde is then added to the antigen-dissolved chitosan mixture such that the final concentration is 0.2% formaldehyde or 0.008 M formaldehyde. In the Examples above, a 37% solution of formaldehyde is used. Tris-HCl can be added to a final concentration 0.5 g/L.

Preparation of Mannosylated Chitosan:

Two molar equivalents of mannose in one volume of 0.1 M sodium acetate, pH 4.0 were heated at 60° C. for two hours. The solution was then added to two volumes of one molar equivalent of 2% chitosan in 0.15% acetic acid and allowed to react for 10 min at room temperature to produce a 1.5% mannosylated chitosan solution. This can then be mixed with broth cultures such that 2 volumes of culture are mixed with one volume of 1.5% mannosylated chitosan. Concentrated antigens can be diluted as minimal as possible or as desired. Tris-HC can be added to a final concentration 0.5 g/L.

We claim:

1. A method of enhancing the immune response to a vaccine in a mammalian subject or a poultry subject comprising administering to said subject an effective amount of an adjuvant composition comprising a carbohydrate linked to chitosan to form a Schiff base, wherein the carbohydrate is an open ring mannose moiety and an effective amount of a vaccine composition comprising an antigen, wherein the difference in administration time for the administration of the adjuvant composition and the administration of the vaccine composition is between 1 hour and 25 days.

2. The method of claim 1, wherein the difference in the administration time is at least one hour, 2 hours, 4 hours, 8 hours, 12 hours, 16 hours, 20 hours, one day, 2 days, 4 days, 7 days, or 2 weeks.

3. The method of claim 1, wherein the adjuvant composition is administered before the vaccine composition.

4. The method of claim 1, wherein the adjuvant composition is administered after the vaccine composition.

5. The method of claim 1, wherein the Schiff base is not reduced.

6. The method of claim 1, wherein the Schiff base is reduced.

7. The method of claim 1, wherein the adjuvant composition is formulated for mucosal administration.

8. The method of claim 1, wherein the administering of the adjuvant composition is by subcutaneous or mucosal route.

9. The method of claim 1, wherein the administering of the adjuvant composition is administered via food or drinking water.

10. The method of claim 1, wherein the antigen is a protein antigen.

11. The method of claim 10, wherein the protein antigen is *Influenza* M2e, *Influenza* Hemagglutinin, *Influenza* Neuraminidase, or *Influenza* nuclear protein; *Eimeria* TRAP or *Eimeria* MPP; or *Clostridium* sialidase, SagA, alpha-toxin, NetB toxin, or iron transport protein.

12. The method of claim 2, wherein the antigen is a microbe.

13. The method of claim 12, wherein the microbe is *Salmonella, Escherichia, Shigella, Bordetella, Clostridium, Mycoplasma, Staphylococcus, Streptococcus, Bacillus, Influenza,* or *Eimeria*.

14. The method of claim 12, wherein the microbe is inactivated or killed.

15. The method of claim 12, wherein the microbe is a microbe that is killed using formaldehyde, glutaraldehyde, or formalin.

16. The method of claim 1, wherein the mammalian subject is a domestic animal.

17. The method of claim 1, wherein the poultry subject is a chicken or turkey.

* * * * *